(12) United States Patent
Kumar et al.

(10) Patent No.: US 6,838,581 B2
(45) Date of Patent: Jan. 4, 2005

(54) PROCESS FOR THE PREPARATION OF ENANTIOMERICALLY PURE 3-PHENYL-3-HYDROXYPROPYLAMINE

(75) Inventors: Pradeep Kumar, Pune (IN); Rajesh Kumar Pandey, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/309,010

(22) Filed: Dec. 4, 2002

(65) Prior Publication Data

US 2004/0110985 A1 Jun. 10, 2004

(51) Int. Cl.⁷ ............................................. C07C 213/02
(52) U.S. Cl. ...................................................... 564/418
(58) Field of Search ......................................... 564/418

(56) References Cited

PUBLICATIONS

Database CASREACT on STN, Acc. No. 106:84441, Annuziata et al., Journal of the Chemical Society, Perkin Transactions 1: Organic and Bio–Organic Chemistry (1972–1999) (1985), 11, p. 2289–92 (abstract).*

Pandey et al., Tetrahedron Letters 43 (2002), p. 4425–4426.*

* cited by examiner

Primary Examiner—Brian Davis
(74) Attorney, Agent, or Firm—Birch, Stewart, Kolasch & Birch, LLP

(57) ABSTRACT

The present invention relates to an improved process for the synthesis of enantiomerically pure 3-phenyl-3-hydroxypropylamine of formula I; more particularly the present invention relates to the said process using styrene;

FORMULA 1

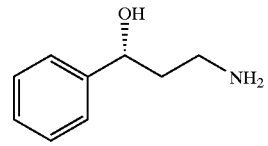

the synthetic strategy features a Sharpless asymmetric dihydroxylation (SAD) route to the target compound, using styrene, a readily accessible starting material gives the optically pure dihydroxy compound (ee >97%; the selective monotosylation of primary alcohol, nucleophilic displacement by cyano and subsequent reduction to amino group furnishes the desired 3-phenyl-3-hydroxypropylamine in enatiomerically pure form, a key intermediate in the synthesis of variety of oxetine related anti-depressant drugs.

16 Claims, No Drawings

PROCESS FOR THE PREPARATION OF ENANTIOMERICALLY PURE 3-PHENYL-3-HYDROXYPROPYLAMINE

FIELD OF THE INVENTION

The present invention relates to an improved process for the synthesis of enantiomerically pure 3-phenyl-3-hydroxypropylamine of formula I.

FORMULA 1

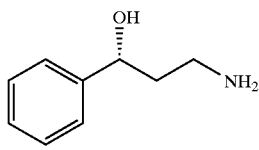

More particularly the present invention relates to the said process using styrene.

BACKGROUND AND PRIOR ART REFERENCES

3-Phenyl-3-hydroxypropylamine is an important intermediate for the synthesis of a variety of antidepressant drugs such as fluoxetine, tomoxetine and nisoxetine etc. Fluoxetine, tomoxetine and nisoxetine are among the most important pharmaceuticals for the treatment of psychiatric disorders (depression, anxiety, alcoholism) and also metabolic problems (obesity and bulimia) [(a) Zerbe, R. L.; Rowe, H.; Enas, G. G.; Wong, D.; Farid, N.; Lemberger, L. J. Pharmacol. Exp. Ther. 1985, 232, 139; (b) Stark, P.; Hardison, C. D. Clin. J. Psychiatry 1985, 46, 53; (c) Robertson, D. W.; Jones, N. D.; Swrtzendruber, J. K.; Yang, K. S.; Wang, D. T. J. Med. Chem. 1988, 31, 185; (d) Robertson, D. W.; Krushinski, J. H.; Fuller, R. W.; Leander, J. D. J. Med. Chem. 1988, 31, 1412].

In the prior-art the synthesis of 3-phenyl-3-hydroxypropylamine segment of fluoxetine and related analogues has been accomplished employing various synthetic strategies. A commonly used strategy for the synthesis of N-methyl-3-phenyl-3-hydroxypropylamine is to employ the reduction of ethylbenzoylacetate with a metal hydride followed by amidation, (G. Magnone, EP 380924, 8 Aug. 1990; Kumar, A. et al Tetrahedron Lett 1991, 32, 1901; Kumar, A. et al Indian J. Chem 1992, 31B, 803; Chenevert, R. et al Tetrahedron 1992, 48, 6769), enzymatic reduction of ethyl benzoylacetate with a chiral ligand e.g. (−)-DIP-chloride (Hilborn, J. W. U.S. Pat. No. 5,936,124, 1999).

In another prior-art method, N-methyl-3-phenyl-3-hydroxypropylamine can be obtained from asymmetric reduction of β-chloropropiophenone with $BH_3$ and chiral oxazoborolidine and subsequent substitution with methyl amine (Corey, E. J. et al Tetrahedron Lett 1989, 30, 5207).

In yet another prior-art method, N-methyl-3-phenyl-3-hydroxypropylamine was obtained by enzymatic resolution process of β-chloropropiophenone and subsequent substitution with methylamine (Schneider, M. P. et al Tetrahedron Asymmetry 1992, 3, 525).

In still another prior-art method, N-methyl-3-phenyl-3-hydroxypropylamine was obtained by asymmetric epoxidation of cinnamyl alcohol and regioselective reductive opening of epoxide with Red-Al (Sharpless K. B. et al J. Org. Chem. 1988, 53, 4081; Young, J. W. WO92-US888, 1992, US-91-793036, 1991).

In another prior-art method, 3-phenyl-3-hydroxypropylamine was obtained by the reduction of 3-phenyl-3-hydroxypropanenitrile (Koenig, T. M. et al Tetrahedron Lett. 1994, 35, 1339; Mitchell D. et al Synth. Commun. 1995, 25, 1231).

In yet another prior-art method, 3-phenyl-3-hydroxypropylamine was obtained by asymmetric hydrogenation of β-aminoketone catalyzed by cationic Rhodium (1) {AMPP} complex (Devocelle, M. et al Synlett 1997,1307).

In still another prior-art method, 3-phenyl-3-hydroxypropylamine was obtained by the asymmetric reduction of methyl-3-benzoylpropionate and subsequent conversion of product to amide and Hoffman rearrangement (Hilborn, J. M. Tetrahedron Lett. 2001, 42, 8919).

Tomoxetine has been prepared via reduction of phenyl haloalkyl ketones with diisopinocamphenyl haloboranes as key steps. The intermediate phenyl haloalkylketone was prepared in 75% yield and 97% ee (Brown, H. C. et. al U.S. Pat. No. 4,868,344, 1989; J. Org. Chem. 1988, 53, 2916). The same intermediate was prepared by Baker's yeast reduction and was further used for the synthesis of (R)-fluoxetine and (R)- and (S)-fenfluramine (Fronza, G. et. al J. Org. Chem., 1991, 56, 6019). In another prior-art method, fluoxetine hydrochloride is manufactured catalytically by hydrogenating 2-benzoyl-N-benzyl-N-methylethylamine in ethylacetate under H pressure of 5 bar using Pt/C or Pd-Pt/C catalyst as key step (Kairisalo, P. J. FI 81083, 1990).

In yet another prior-art method, the (S)-3-amino-1-phenyl-propanol was prepared by the reaction of (S)-1-phthalimido-1-phenyl-propanol and anhydrous $N_2H_4$ in ethanol. This intermediate was subsequently used for the synthesis of fluoxetine derivatives (Fuller, R. W. et al EP 369685, 1990).

In still another prior-art method, the N-methyl-3-phenyl-3-hydroxypropylamine was prepared by the condensation of $PhCH(OH)CH_2CH_2NMe_2$ with $ClCO_2Et$ and subsequent hydrolysis (Schwartz, E. EP 529842, 1993).

In prior-art method, the optically active fluoxetine was prepared employing N-methyl-3-phenyl-3-hydroxypropionamide as a precursor which in turn was prepared by lipase catalyzed resolution of $PhCH(OH)CH_2COOEt$ (Yashida, N. Jpn. Kokai Tokkyo Koho JP 04005268, 1992).

Fluoxetine and its analogs are prepared by the etherification of 1-phenyl-3-(N-methylamino)-propan-1-ol with an arylating reagent (Agusti Cruz, A. ES 2120368, 1998; Arosio, R. U.S. Pat. No. 5,847,214, 1998).

In yet another prior-art method, N-methyl-3R-hydroxy-3-phenylpropylamine was prepared by resolving the racemic by S-(+)-mandelic acid (Ratz, A. M. EP 909754, 1999).

In still another prior-art method, 3-(methylamino)-1-phenyl-1-propanol was prepared by reaction of methylamine with 3-chloro-1-phenyl-1-propanol and subsequently converting into fluoxetine (Weber, B. WO 2000037425, 2000) or by converting chloropropiophenone into racemic alcohol and resolving it by the chiral separation (Gattuso, M. J. Jpn. Kokai Tokkyo Koho JP 2000290239, 2000).

Some of the major drawbacks of the methods known in the prior-art are such as:

(i) Multi-step synthesis
(ii) High cost of materials involved
(iii) Complicated reagents, longer reaction time and high reaction temperature
(iv) Difficulties involved in work-up procedure
(v) Difficulties involved in handling sophisticated reagents (vi) Overall low yield of the desired compound
(vii) Poor enantio-selectivity
(viii) Lack of reusability of expensive reagents In view of the abovementioned drawbacks and disadvantages of the prior-art procedure, it is desirable to develop an improved, efficient and enantioselective process for the synthesis of 3-phenyl-3-hydroxypropylamine.

OBJECTS OF THE INVENTION

The main object of the present invention is to provide an improved, efficient process for the synthesis of enantiomerically pure 3-phenyl-3-hydroxy-propylamine, which overcomes the drawbacks of the prior-art processes employing the Sharpless asymmetric dihydroxylation, selective monotosylation of primary alcohol and nucleophilic displacement by cyano and subsequent reduction to amino group.

Another object of the invention is to provides a process of synthesizing enantiomerically pure 3-phenyl-3-hydroxy-propylamine using chiral ligands to induce chirality.

Another object is to synthesis of enantiomerically pure 3-phenyl-3-hydroxy-propylamine relatively at lower temperature or room temperature In yet another object of the invention is to provide a process of preparing both the enantiomers of 3-phenyl-3-hydroxypropylamine.

SUMMARY OF THE INVENTION

Accordingly, the present invention provides a process of improved process for the synthesis of enantiomerically pure 3-phenyl-3-hydroxypropylamine of formula I.

FORMULA 1

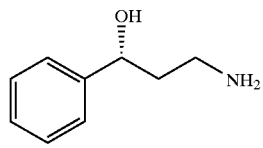

More particularly the present invention relates to the said process using styrene for producing enantiomerically pure 3-phenyl-3-hydroxypropylamine of formula I.

DETAILED DESCRIPTION OF THE INVENTION

In accordance to the objectives of the present invention, the said process is described in details in schematic diagram herein below

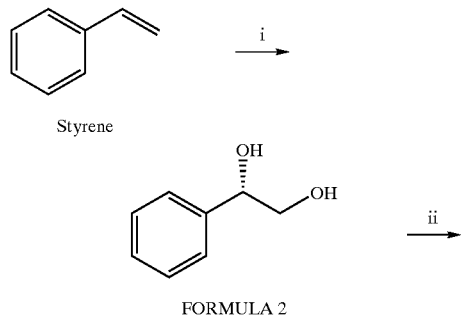

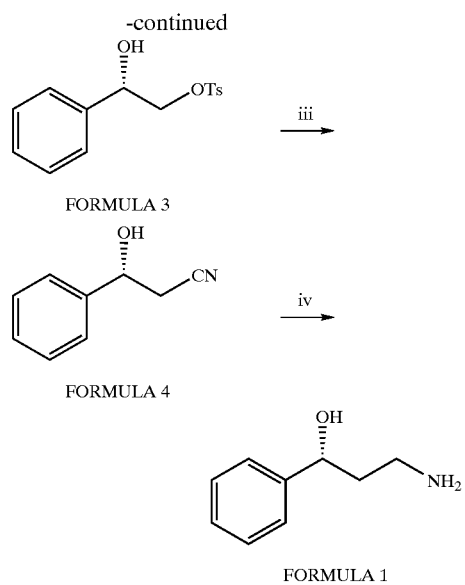

Accordingly, the present invention provides an improved process for the preparation of enantiomerically pure 3-phenyl-3-hydroxy propyl amine, said process comprising the steps of:

i) adding osmium tetraoxide to a mixture of potassium ferricyanide, potassium carbonate, chiral ligand in an aqueous organic solvent at a temperature in the range of 0 to 5° C.;

ii) stirring the mixture obtained in step (i) with styrene at a temperature in the range of 0 to 5° C. for 12 to 24 hours and then quenching with solid sodium sulfite;

iii) further stirring the contents of step (ii) for a period range of 30 minutes to 2 hours and extracting with ethylacetate repeatedly;

iv) washing the combined ethylacetate extracts with brine, drying over anhydrous $Na_2SO_4$, filtering and concentrating to obtain a crude product;

v) purifying the crude product obtained in step (iv) over silica-gel column using a proportionate mixture of petroleum ether and ethyl acetate to obtain pure chiral diol compound of formula (2);

vi) reacting chiral diol of formula (2) with an activating reagent portion wise in presence of a base stirring it for a period in the range of 15 to 24 hours at a temperature range of −40° C. to 35° C. and then quenching to obtain compound of formula (3);

vii) reacting compound of formula (3) obtained from step (vi) with a metal cyanide in an aqueous alcohol at room temperature for a period of 15 to 24 hours, concentrating it at a temperature range of 40–70° C., extracting with brine, drying over anhydrous $Na_2SO_4$, purifying it over silica gel column to obtain a pure chiral cyano compound of formula (4); and viii) reducing the compound of formula (4) obtained from step (vii) with a reducing agent at −15 to 0° C., refluxing for a period of 1–3 hours, extracting the mixture with an organic solvent and then concentrating to obtain the product of formula (1).

An embodiment of the present invention provides a process, wherein the chiral ligand used may be one of the $1^{st}$ or $2^{nd}$ generation mono- or bi-dentate ligands selected from a group consisting of phthalazine, pyrimidine, phenanthryl, quinoxaline, p-chlorobenzoate, preferably phthalazine.

Another embodiment of the present invention, the ratio of activating agent to chiral diol (2) used is in the range of 1:5–5:1.

In still another embodiment, the organic solvent used in step (i) is preferably toluene.

In yet another embodiment, the ratio of petroleum ether to ethyl acetate used in step (v) ranges from 4:1 to 2:1.

In yet another embodiment, the activating reagent used in step (vi) is selected from a group consisting of acid chloride, anhydride, and sulfonyl chloride like p-toluene sulfonyl chloride, methane sulfonyl chloride preferably p-toluene sulfonyl chloride.

In yet another embodiment, wherein the base used in step (vi) is selected from a group consisting of triethylamine and pyridine.

In yet another embodiment, the quenching agent used in step (vi) is preferably water.

In yet another embodiment, the metal cyanide used in (vii) is an alkali or alkaline earth metal cyanide, preferably sodium cyanide.

In yet another embodiment, the aqueous alcohol used in step (vii) is preferably ethanol.

In yet another embodiment, the organic solvent used in step (viii) is preferably dichloromethane.

In yet another embodiment, the reducing agent used in (viii) is selected from a group consisting of dimethyl sulfide complex neat or THF solution, hydrides of alkali metals exemplified by sodium borohydride, lithium borohydride, lithium aluminum hydride, sodium cyanoborohydride and Raney Ni preferably borane-dimethyl sulfide complex/lithium aluminum hydride.

The 3-phenyl-3-hydroxypropylamine may be used to obtain O-arylated compounds, intermediates for the preparation of fluoxetine, tomoxetine and nisoxetine by reacting it with an arylating reagent as an electrophile in the presence of a base at ambient temperature.

In a feature of the present invention in order to make both the enantiomer of the 3-phenyl-3-hydroxypropylamine, a variety of ligands used in Sharpless asymmetric dihydroxylation procedure were procured from Aldrich Co.

The present invention provides an improved highly enantioselective synthesis of 3-phenyl-3-hydroxypropylamine. The synthetic strategy features a Sharpless asymmetric dihydroxylation (SAD) route to the target compound. The Sharpless asymmetric dihydroxylation of styrene, a readily accessible starting material gives the optically pure dihydroxy compound (ee >97%). The selective monotosylation of primary alcohol, nucleophilic displacement by cyano and subsequent reduction to amino group furnishes the desired 3-phenyl-3-hydroxypropylamine in enantiomerically pure form, a key intermediate in the synthesis of variety of oxetine related anti-depressant drugs.

The process of the present invention is described herein below with examples, which are illustrative only and should not be construed to limit the scope of present invention in any manner.

EXAMPLE 1

To a mixture of $K_3Fe(CN)_6$, $K_2CO_3$ and $(DHQ)_2PHAL$ in t-BuOH—$H_2O$ (1:1) cooled to 0° C. was added $OsO_4$ (0.1 M solution in toluene). After stirring for 5 minutes at 0° C., styrene was added in one portion. The reaction mixture was stirred at 0° C. for 24 h and then quenched with solid sodium sulfite. The stirring was continued for 1 h and the solution was extracted with ethyl acetate. The combined organic phase was washed with brine, dried ($Na_2SO_4$) and concentrated. Silica gel column chromatography of crude product using petroleum ether:EtOAc (3.5:1.5) as eluent gave (R)-phenylethylene glycol as a white solid.

To a mixture of (R)-phenylethylene glycol, dry pyridine in dry dichloromethane cooled at −15° C. was added portion wise p-toluenesulfonyl chloride over a period of 1 h. The reaction was stirred at −15° C. for 24 h and quenched by adding water. The solution was extracted with dichloromethane and then combined organic phase was washed with aqueous $CuSO_4$, dried ($Na_2SO_4$) and concentrated. Silica gel column chromatography of crude product using petroleum ether:EtOAc (4:1) as eluent gave monotosyl compound as a white solid.

To stirring mixture of monotosyl compound in ethanol-$H_2O$ (4:1) at 0° C. was added NaCN in one portion. The reaction mixture was stirred at room temperature for 24 h. The reaction mixture was concentrated at 50° C. on rotatory evaporator and extracted with ethyl acetate. The combined organic phases were washed with brine, dried ($Na_2SO_4$) and concentrated. Silica gel column chromatography of crude product using petroleum ether:EtOAc (3:1) as eluent gave (R)-3-phenyl-3-hydroxypropanenitrile (4) as a colorless oil.

To a THF solution of (R)-3-phenyl-3-hydroxypropanenitrile was slowly added borane dimethyl sulfide complex at room temperature. Methyl sulfide was then distilled from the reaction vessel and the resulting THF solution refluxed for 2.5 h. After cooling to room temperature methanolic HCl was added to the reaction mixture. Methanol and methyl borate were removed by distillation and the reaction mixture neutralized with sodium hydroxide (5N). Extraction of the mixture with dichloromethane followed by concentration provided the crystalline (R)-3-phenyl-3-hydroxypropylamine.

EXAMPLE 2

To a mixture of $K_3Fe(CN)_6$, $K_2CO_3$ and $(DHQ)_2PHAL$ in t-BuOH—$H_2O$ (1:1) cooled to 0° C. was added $OsO_4$ (0.1 M solution in toluene). After stirring for 5 minutes at 0° C., styrene was added in one portion. The reaction mixture was stirred at 0° C. for 24 h and then quenched with solid sodium sulfite. The stirring was continued for 1 h and the solution was extracted with ethyl acetate. The combined organic phase was washed with brine, dried ($Na_2SO_4$) and concentrated. Silica gel column chromatography of crude product using petroleum ether:EtOAc (3.5:1.5) as eluent gave (R)-phenylethylene glycol as a white solid.

To a mixture of (R)-phenylethylene glycol, dry triethylamine in dry dichloromethane cooled at −15° C. was added portion wise methanesulfonyl chloride over a period of 1 h. The reaction was stirred at −15° C. for 24 h and quenched by adding water. The solution was extracted with dichloromethane and then combined organic phase was washed with aqueous $CuSO_4$, dried ($Na_2SO_4$) and concentrated. Silica gel column chromatography of crude product using petroleum ether:EtOAc (4:1) as eluent gave monomesyl compound as a white solid.

To stirring mixture of monomesyl compound in ethanol-$H_2O$ (4:1) at 0° C. was added KCN in one portion. The reaction mixture was stirred at room temperature for 24 h. The reaction mixture was concentrated at 50° C. on rotatory evaporator and extracted with ethyl acetate. The combined organic phases were washed with brine, dried ($Na_2SO_4$) and concentrated. Silica gel column chromatography of crude product using petroleum ether:EtOAc (3:1) as eluent gave (R)-3-phenyl-3-hydroxypropanenitrile (4) as a colorless oil.

To a THF solution of (R)-3-phenyl-3-hydroxypropanenitrile was slowly added borane THF complex at room temperature and then the resulting solution was refluxed for 2.5 h. After cooling to room temperature methanolic HCl was added to the reaction mixture. Methanol and methyl borate were removed by distillation and the reaction mixture neutralized with sodium hydroxide (5N). Extraction of the mixture with dichloromethane,followed by concentration provided the crystalline (R)-3-phenyl-3-hydroxypropylamine.

EXAMPLE 3

To a mixture of $K_3Fe(CN)_6$, $K_2CO_3$ and $(DHQ)_2PHAL$ in t-BuOH—$H_2O$ (1:1) cooled to 0° C. was added $OsO_4$ (0.1 M solution in toluene). After stirring for 5 minutes at 0° C., styrene was added in one portion. The reaction mixture was stirred at 0° C. for 24 h and then quenched with solid sodium sulfite. The stirring was continued for 1 h and the solution was extracted with ethyl acetate. The combined organic phase was washed with brine, dried ($Na_2SO_4$) and concentrated. Silica gel column chromatography of crude product using petroleum ether:EtOAc (3.5:1.5) as eluent gave (R)-phenylethylene glycol as a white solid.

To a mixture of (R)-phenylethylene glycol, dry pyridine in dry dichloromethane cooled at −15° C. was added portion wise p-toluenesulfonyl chloride over a period of 1 h. The reaction was stirred at −15° C. for 24 h and quenched by adding water. The solution was extracted with dichloromethane and then combined organic phase was washed with aqueous $CuSO_4$, dried ($Na_2SO_4$) and concentrated. Silica gel column chromatography of crude product using petroleum ether:EtOAc (4:1) as eluent gave monotosyl compound as a white solid.

To stirring mixture of monotosyl compound in ethanol-$H_2O$ (4:1) at 0° C. was added NaCN in one portion. The reaction mixture was stirred at room temperature for 24 h. The reaction mixture was concentrated at 50° C. on rotatory evaporator and extracted with ethyl acetate. The combined organic phases were washed with brine, dried ($Na_2SO_4$) and concentrated. Silica gel column chromatography of crude product using petroleum ether:EtOAc (3:1) as eluent gave (R)-3-phenyl-hydroxypropanenitrile as a colorless oil.

To a stirring suspension of lithium aluminum hydride in dry THF at 0° C. was added a solution of (R)-3-phenyl-3-hydroxypropanenitrile in dry THF under nitrogen. The ice bath was removed and then the reaction mixture was refluxed for 2 h. Excess lithium aluminum hydride was destroyed by adding $H_2O$ and EtOAc. The white precipitate obtained was filtered and washed with MeOH. The combined filtrate was concentrated to give (R)-3-phenyl-3-hydroxypropylamine.

EXAMPLE 4

To a mixture of $K_3Fe(CN)_6$, $K_2CO_3$ and $(DHQ)_2PHAL$ in t-BuOH—$H_2O$ (1:1) cooled to 0° C. was added $OsO_4$ (0.1 M solution in toluene). After stirring for 5 minutes at 0° C., styrene was added in one portion. The reaction mixture was stirred at 0° C. for 24 h and then quenched with solid sodium sulfite. The stirring was continued for 1 h and the solution was extracted with ethyl acetate. The combined organic phase was washed with brine, dried ($Na_2SO_4$) and concentrated. Silica gel column chromatography of crude product using petroleum ether:EtOAc (3.5:1.5) as eluent gave (R)-phenylethylene glycol as a white solid.

To a mixture of (R)-phenylethylene glycol, dry pyridine in dry dichloromethane cooled at −15° C. was added portion wise p-toluenesulfonyl chloride over a period of 1 h. The reaction was stirred at −15° C. for 24 h and quenched by adding water. The solution was extracted with dichloromethane and then combined organic phase was washed with aqueous $CuSO_4$, dried ($Na_2SO_4$) and concentrated. Silica gel column chromatography of crude product using petroleum ether:EtOAc (4:1) as eluent gave monotosyl compound as a white solid.

To stirring mixture of monotosyl compound in ethanol-$H_2O$ (4:1) at 0° C. was added KCN in one portion. The reaction mixture was stirred at room temperature for 24 h. The reaction mixture was concentrated at 50° C. on rotatory evaporator and extracted with ethyl acetate. The combined organic phases were washed with brine, dried ($Na_2SO_4$) and concentrated. Silica gel column chromatography of crude product using petroleum ether:EtOAc (3:1) as eluent gave (R)-3-phenyl-hydroxypropanenitrile as a colorless oil.

To a THF solution of (R)-3-phenyl-3-hydroxypropanenitrile was slowly added borane dimethyl sulfide complex at room temperature. Methyl sulfide was then distilled from the reaction vessel and the resulting THF solution refluxed for 2.5 h. After cooling to room temperature methanolic HCl was added to the reaction mixture. Methanol and methyl borate were removed by distillation and the reaction mixture neutralized with sodium hydroxide (5N). Extraction of the mixture with dichloromethane followed by concentration provided the crystalline (R)-3-phenyl-3-hydroxypropylamine.

EXAMPLE 5

To a mixture of $K_3Fe(CN)_6$, $K_2CO_3$ and $(DHQD)_2PHAL$ in t-BuOH—$H_2O$ (1:1) cooled to 0° C. was added $OsO_4$ (0.1 M solution in toluene). After stirring for 5 minutes at 0° C., styrene was added in one portion. The reaction mixture was stirred at 0° C. for 24 h and then quenched with solid sodium sulfite. The stirring was continued for 1 h and the solution was extracted with ethyl acetate. The combined organic phase was washed with brine, dried ($Na_2SO_4$) and concentrated. Silica gel column chromatography of crude product using petroleum ether:EtOAc (3.5:1.5) as eluent gave (S)-phenylethylene glycol as a white solid.

To a mixture of (S)-phenylethylene glycol, dry triethylamine in dry dichloromethane cooled at −15° C. was added portion wise p-toluenesulfonyl chloride over a period of 1 h. The reaction was stirred at −15° C. for 24 h and quenched by adding water. The solution was extracted with dichloromethane and then combined organic phase was washed with aqueous $CuSO_4$, dried ($Na_2SO_4$) and concentrated. Silica gel column chromatography of crude product using petroleum ether:EtOAc (4:1) as eluent gave monotosyl compound as a white solid.

To stirring mixture of monotosyl compound in ethanol-$H_2O$ (4:1) at 0° C. was added NaCN in one portion. The reaction mixture was stirred at room temperature for 24 h. The reaction mixture was concentrated at 50° C. on rotatory evaporator and extracted with ethyl acetate. The combined organic phases were washed with brine, dried ($Na_2SO_4$) and concentrated. Silica gel column chromatography of crude product using petroleum ether:EtOAc (3:1) as eluent gave (S)-3-phenyl-hydroxypropanenitrile as a colorless oil.

To a THF solution of (S)-3-phenyl-3-hydroxypropanenitrile was slowly added THF solution of borane dimethyl sulfide complex at room temperature. Methyl sulfide was then distilled from the reaction vessel and the resulting THF solution refluxed for 2.5 h. After cooling to room temperature methanolic HCl was added to the reaction mixture. Methanol and methyl borate were removed by distillation and the reaction mixture neutralized with sodium hydroxide (5N). Extraction of the mixture with dichloromethane, followed by concentration provided the crystalline (S)-3-phenyl-3-hydroxypropylamine.

The advantages of the present invention are as follows:
(i) the process relatively involves less number of steps.
(ii) the reactions involved in each step, according to the present invention, could be carried out lower temperature or room temperature.
(iii) the process leads to high yields of the desired products.
(iv) Both the enantiomers of the 3-phenyl-3-hydroxypropylamine could be prepared using this process.
(v) the process gives high enantioselectivity of the product.
(vi) the chiral ligands used to induce chirality could be recovered.

We claim:
1. A process for the preparation of enantiomerically pure 3-phenyl-3-hydroxy propyl amine, said process comprising the steps of:
   i. adding osmium tetraoxide to a mixture of potassium ferricyanide, potassium carbonate, chiral ligand in an aqueous organic solvent at a temperature in the range of 0 to 5° C.;
   ii. stirring the mixture obtained in step (i) with styrene at a temperature in the range of 0 to 5° C. for 12 to 24 hours and then quenching with solid sodium sulfite;
   iii. further stirring the contents of step (ii) for a period range of 30 minutes to 2 hours and extracting with ethyl acetate repeatedly;
   iv. washing the combined ethyl acetate extracts with brine, drying over anhydrous Na$_2$SO$_4$, filtering and concentrating to obtain a crude product;
   v. purifying the crude product obtained in step (iv) over silica-gel column using a proportionate mixture of petroleum ether and ethyl acetate to obtain pure chiral diol compound of formula (2);

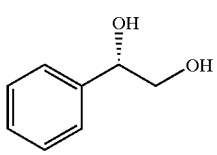

FORMULA 2 vi. reacting chiral diol of formula (2) with an activating reagent portion wise in presence of a base stirring it for a period in the range of 15 to 24 hours at a temperature range of −40° C. to 35° C. and then quenching to obtain compound of formula (3);

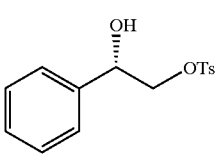

FORMULA 3 vii. reacting compound of formula (3) obtained from step (vi) with a metal cyanide in an aqueous alcohol at room temperature for a period of 15 to 24 hours, concentrating it at a temperature range of 40–70° C., extracting with brine, drying over anhydrous Na$_2$SO$_4$, purifying it over silica gel column to obtain a pure chiral cyano compound of formula (4);

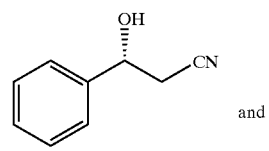

FORMULA 4 and viii. reducing the compound of formula (4) obtained from step (vii) with a reducing agent at −15 to 0° C., refluxing for a period of 1–3 hours, extracting the mixture with an organic solvent and then concentrating to obtain the product of formula (1)

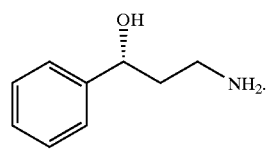

FORMULA 1

2. A process as claimed in claim 1, wherein the chiral ligand is at least one of the $1^{st}$ or $2^{nd}$ generation mono- or bi-dentate ligands selected from a group consisting of phthalazine, pyrimidine, phenanthryl, quinoxaline, p-chlorobenzoate.

3. A process as claimed in claim 1, wherein the ratio of activating agent to chiral diol (2) is in the range of 1:5–5:1.

4. A process as claimed in claim 1, wherein the organic solvent used in step (i) is toluene.

5. A process as claimed in claim 1, wherein in step (v), the ratio of petroleum ether to ethyl acetate ranges from 4:1 to 2:1.

6. A process as claimed in claim 1, wherein the activating reagent used in step (vi) is at least one selected from a group consisting of acid chloride, anhydride, and sulfonyl chloride.

7. A process as claimed in claim 1, wherein the base used in step (vi) is at least one selected from a group consisting of triethylamine and pyridine.

8. A process as claimed in claim 1, wherein the quenching agent used in step (vi) is water.

9. A process as claimed in claim 1, wherein the metal cyanide used in step (vii) is an alkali or alkaline earth metal cyanide.

10. A process as claimed in claim 1, wherein the aqueous alcohol used in step (vii) is ethanol.

11. A process as claimed in claim 1, wherein the organic solvent used in step (viii) is dichloromethane.

12. A process as claimed in claim 1, wherein the reducing agent used in step (viii) is at least one selected from a group consisting of neat dimethyl sulfide complex, THF solution dimethyl sulfide complex, and hydrides of alkali metals.

13. A process as claimed in claim 2, wherein the chiral ligand is phthalazine.

14. A process as claimed in claim 6, wherein the activating reagent is at least one selected from the group consisting of p-toluene sulfonyl chloride and methane sulfonyl chloride.

15. A process as claimed in claim 1, wherein the reducing agent used in step (viii) is at least one selected from the group consisting of sodium borohydride, lithium borohydride, lithium aluminum hydride, sodium cyanoborohydride and Raney Ni.

16. A process as claimed in claim 12, wherein the reducing agent is at least one selected from the group consisting of borane-dimethyl sulfide complex and lithium aluminum hydride.

* * * * *